United States Patent
Claverie et al.

(10) Patent No.: US 7,078,363 B2
(45) Date of Patent: Jul. 18, 2006

(54) OLEFIN POLYMERISATION CATALYST

(75) Inventors: Jerôme Claverie, Dover, NH (US); Rémi Soula, Saint-Priest (FR); Roger Spitz, Lyons (FR)

(73) Assignee: Arkema, Puteaux (FR)

( * ) Notice: Subject to any disclaimer, the term of this patent is extended or adjusted under 35 U.S.C. 154(b) by 199 days.

(21) Appl. No.: 10/380,698

(22) PCT Filed: Sep. 17, 2001

(86) PCT No.: PCT/FR01/02881

§ 371 (c)(1), (2), (4) Date: Jul. 10, 2003

(87) PCT Pub. No.: WO02/24763

PCT Pub. Date: Mar. 28, 2002

(65) Prior Publication Data

US 2004/0097672 A1 May 20, 2004

(30) Foreign Application Priority Data

Sep. 19, 2000 (FR) .................................. 00 11950

(51) Int. Cl.
- B01J 31/38 (2006.01)
- C08F 4/72 (2006.01)

(52) U.S. Cl. ...................... 502/155; 502/167; 526/161; 526/171; 526/172; 526/348; 526/351; 526/352

(58) Field of Classification Search ................ 502/155, 502/167; 526/161, 171, 172, 348, 351, 352
See application file for complete search history.

(56) References Cited

U.S. PATENT DOCUMENTS

| | | | |
|---|---|---|---|
| 3,635,937 A | 1/1972 | Bauer et al. | |
| 3,637,636 A | 1/1972 | Bauer et al. | |
| 3,647,914 A | 3/1972 | Glockner et al. | |
| 3,661,803 A | 5/1972 | Bauer et al. | |
| 3,686,159 A | 8/1972 | Bauer et al. | |
| 4,293,727 A | 10/1981 | Beach et al. | |
| 4,301,318 A | 11/1981 | Beach et al. | |
| 4,529,554 A | 7/1985 | Beach et al. | |
| 4,716,205 A | 12/1987 | Klabunde | |
| 5,929,181 A | 7/1999 | Makovetsky et al. | |
| 6,197,984 B1 | 3/2001 | Makovetsky et al. | |

FOREIGN PATENT DOCUMENTS

| BG | 60319 | 7/1994 |
|---|---|---|
| FR | 2 784 110 | 4/2000 |
| FR | 2814169 | 3/2002 |
| WO | WO 98/56837 | * 12/1998 |

OTHER PUBLICATIONS

Klabunde U., et al., "Reaction of nickel polymerization catalysts with carbon monoxide", J. Organomet. Chem. (1987), 334 (1-2), 141-56, XP-001002462.

Jacobson S. et al. "Nucleophilic Attach on Co-ordinated Phosphinoacetylenes: Products from the Hydrolysis of Cis-PDC12 (PH2PC CCF3) and the X-Ray Structure of a 1-Diphenylphosphino-3, 3, 3-Trifluoropropen-2-Olato Complex", Journal of the Chemical Society, Chemical Communicatins, Chemical Society. Letchworth, GB, No. 7, 1974, pp. 668-669, XP001002443 ISSN: 0022-4936.

Mueller, Ulrich, et al. "Ph2PCH2C (CF3)2O1NiH(Pcy3) (Cy = cyclohexyl): proof of a nickel hydride mechanism of ethane oligomerization", Angew. Chem. (1989), 101(8), 1066-7, XP001006327, p. 1066.

U. Klabunde, et al., "Ethylene Homopolymerization with P, O-Chelated Nickel Catalysts", Journal of Polymer Science, Part A: Polymer Chemistry, vol. 25, pp. 1989-2003 (1987).

U. Klabunde, et al., "Nickel Catalysis for Ethylene Homo-And-Co-Polymerization", Journal of Molecular Catalysis, 41 (1987) pp. 123-134.

A. Held, et al., Coordination Polymerization of Ethylene in Water by Pd(II) and Ni(II) Catalysts, Chem. Comm., (2000), pp. 301-302.

* cited by examiner

Primary Examiner—Robert D. Harlan
(74) Attorney, Agent, or Firm—Smith, Gambrell & Russell, LLP

(57) ABSTRACT

The invention concerns a catalyst for olefin polymerisation, of formula (I) wherein: E is an oxygen or sulphur atom; X is a phosphorus, arsenic or antimony atom; M is a nickel, palladium or platinum atom comprising a non-attributed valency; a is 1 or 2; $R_1$, $R_2$, $R_3$, identical or different can be selected among hydrogen, alkyl, cycloalkyl, aryl, alkylaryl, arylalkyl radicals, the hydroxyl radical, the alkoxide radicals (with 1 to 20 carbon atoms), the groups —C(O)OR'—, —SO$_3$Y; and Z represents a hydrocarbon radical comprising 2 to 3 carbon atoms; R represents a hydrocarbon radical of valency a, provided that at least one of the radicals Z or R bears at least an electroattractive substituent (I)

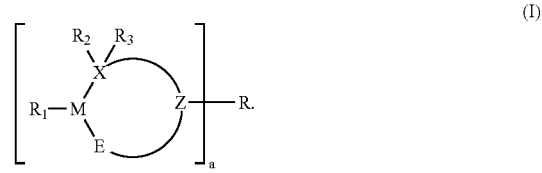

22 Claims, No Drawings

OLEFIN POLYMERISATION CATALYST

FIELD OF THE INVENTION

The present invention relates to the polymerization of olefins, to a catalyst for polymerizing olefins, to a process for preparing such a catalyst and to a process for polymerizing olefins.

BACKGROUND OF THE INVENTION

Polymers of ethylene and other olefins are of major commercial appeal. These polymers have a very large number of uses, ranging from low molecular weight products for lubricants and greases, to higher molecular weight products for manufacturing fibers, films, molded articles, elastomers, etc. In most cases, the polymers are obtained by catalytic polymerization of olefins using a compound based on a transition metal. The nature of this compound has a very strong influence on the properties of the polymer, its cost and its purity. Given the importance of polyolefins, there is a permanent need to improve the catalytic systems in order to propose new systems.

A variety of homogeneous or heterogeneous catalysts for the polymerization or copolymerization of ethylene exists. Among the families that are most widely known, examples that may be mentioned include the "Ziegler"-type catalysts involving organometallic complexes of metals from groups III and IV or "Philipps"-type catalysts involving chromium complexes. However, there are also nickel-based catalysts, which have been used in particular for many years for producing cc-olefins. Certain systems also have a certain level of tolerance toward polar media.

Among the many catalytic systems presented in the literature, examples that have been described include the combination between a nickel complex, such as bis-1,5-cyclooctadiene, with benzoic acid derivatives, for instance 2-mercaptobenzoic acid or 3,5-diaminobenzoic acid (U.S. Pat. No. 3,637,636) or with chelating tertiary organophosphorus ligands (U.S. Pat. No. 3,635,937, U.S. Pat. No. 3,647,914) or alternatively with glycolic, thioglycolic or thiolactic acid (U.S. Pat. No. 3,661,803). U.S. Pat. No. 3,686,159 describes the use of a complex of nickel in oxidation state zero, such as, once again, bis-1,5-cyclooctadiene, with a phosphorus ylide ligand. The above inventions have in common the in situ formation of the active species in the polymerization medium.

Other methods, for instance in American patent U.S. Pat. No. 4,716,205 or Bulgarian patent BG 60319, claim catalytic nickel systems that may be isolated, but it is necessary to introduce into the polymerization medium an acceptor compound capable of extracting one of the ligands from the nickel complex in order to make it active. The in situ technique does not allow the catalytic system to be isolated so as to precisely identify its structure, but the procedure has the merit of being simple and it limits the manipulations of the catalysts, which is a source of contamination.

U.S. Pat. Nos. 4,293,727, 4,301,318 and 4,529,554 relate to ethylene oligomerization processes that involve placing ethylene in contact with nickel ylides comprising sulfonated substituents. These ylides especially have the drawback of being difficult to synthesize.

U.S. Pat. No. 4,716,205 relates to the polymerization of ethylene in the presence of certain nickel-containing catalysts.

In the article entitled "Ethylene Homopolymerization with P,O-Chelated Nickel Catalysts" by U. Klabunde et al., Journal of Polymer Science, Part A: Polymer Chemistry, Vol. 25, 1989–2003 (1987), and also in the article "Nickel catalysis for ethylene homo- and copolymerization" by U. Klabunde and S. D. Ittel, Journal of Molecular Catalysis, 41 (1987), 123–134, catalysts based on phosphorus and nickel are described.

The article entitled "Coordination polymerization of ethylene in water by Pd(II) and Ni(II) catalysts" by A. Held, F. M. Bauers and S. Mecking, Chem. Comm., 2000, 301–302, mentions the polymerization of ethylene in water using nitrogenous palladium (II) complexes and sulfonated nickel (II) complexes.

The French patent application published under No. 2 784 110 concerns a process for polymerizing at least one olefin in the presence of at least one catalyst comprising at least one sequence E-M-X in which E represents an oxygen or sulfur atom, M represents a nickel, palladium or platinum atom, and X represents a phosphorus, arsenic or antimony atom, in a medium comprising a continuous liquid phase which comprises more than 30% by weight of water. The catalyst example cited in said document is the structure represented by formula (1)

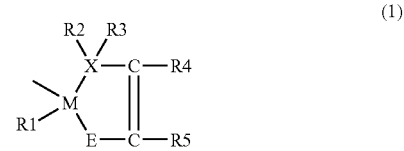

in which the radicals $R_1$, $R^2$, $R^3$, $R^4$ and $R^5$, which may be identical or different, may be chosen from hydrogen, alkyl, cycloalkyl, aryl, alkylaryl or arylalkyl radicals, halogens, the hydroxyl radical, alkoxide radicals, —C(O)OR' in which R' represents a hydrocarbon-based radical that may contain from 1 to 15 carbon atoms, —$SO_3Y$ in which Y is chosen from Li, Na, K, $NH_4^\oplus$, $NR''_4^\oplus$ in which R" represents a hydrocarbon-based radical that may contain from 1 to 15 carbon atoms.

Also mentioned as a catalyst in said document is the structure represented by formula

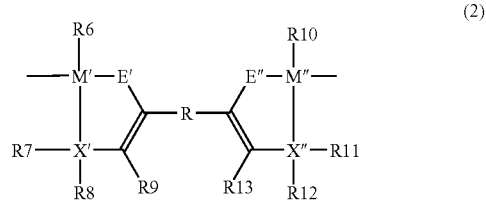

in which the radicals $R^6$, $R^7$, $R^8$, $R^9$, $R^{10}$, $R^{11}$, $R^{12}$ and $R^{13}$, which may be identical or different, may be chosen from the same list of radicals as $R^1$ to $R^5$ above, E'-M'-X' and E"-M"-X" being two sequences of the type E-M-X and may be identical or different, R being a divalent hydrocarbon-based radical. The aim of the invention is to propose a novel catalyst for polymerizing olefins, which has improved activity and production efficiency, even in the presence of a polar medium, given that polar media generally considerably reduce the activity of the catalysts.

The invention also proposes to provide a catalyst that can be prepared in situ.

This catalyst corresponds to the following formula:

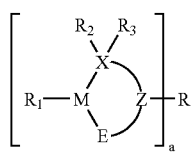

in which:

E is an oxygen or sulfur atom;

X is a phosphorus, arsenic or antimony atom;

M is a nickel, palladium or platinum atom comprising an unattributed valency;

a is 1 or 2;

$R_1$, $R_2$ and $R_3$, which may be identical or different, may be chosen from hydrogen, alkyl, cycloalkyl, aryl, alkylaryl and arylalkyl radicals, each generally containing from 1 to 20 carbon atoms, the hydroxyl radical, alkoxide radicals (with from 1 to 20 carbon atoms), —C(O)OR' in which R' represents a hydrocarbon-based radical that may contain from 1 to 15 carbon atoms, —$SO_3Y$ in which Y is chosen from Li, Na, K, $NH_4^\oplus$, $NR''_4^\oplus$ in which R" represents a hydrocarbon-based radical that may contain from 1 to 15 carbon atoms; and Z represents a hydrocarbon-based radical containing 2 or 3 carbon atoms;

R represents a hydrocarbon-based radical of valency a; on condition that at least one of the radicals Z and R bears at least one electron-withdrawing substituent.

Such a catalyst thus makes it possible to obtain a polyolefin, for instance polyethylene or an ethylene copolymer, of high molecular mass, with very high activity even in the presence of a polar medium.

A subject of the invention is also a process for preparing the catalyst according to the invention, comprising the following reaction, in which L is a ligand:

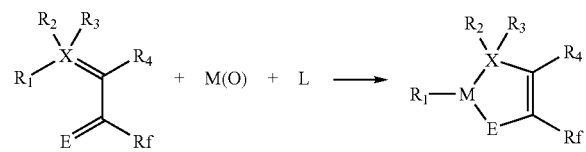

in which E, X, M, Rf and $R_1$, $R_2$, $R_3$ and $R_4$ have the meanings given above.

Another subject of the present invention is a process for polymerizing at least one olefin, which involves placing said olefin(s) in contact with a catalyst according to the invention.

DETAILED DESCRIPTION OF THE INVENTION

Catalyst According to the Invention

The catalyst according to the invention corresponds to the following formula:

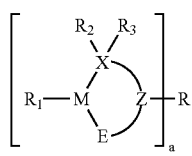

in which:

E is an oxygen or sulfur atom;

X is a phosphorus, arsenic or antimony atom;

M is a nickel, palladium or platinum atom comprising an unattributed valency;

a is 1 or 2;

$R_1$, $R_2$ and $R_3$, which may be identical or different, may be chosen from hydrogen, alkyl, cycloalkyl, aryl, alkylaryl and arylalkyl radicals, each generally containing from 1 to 20 carbon atoms, the hydroxyl radical, alkoxide radicals (with from 1 to 20 carbon atoms), —C(O)OR' in which R' represents a hydrocarbon-based radical that may contain from 1 to 15 carbon atoms, —$SO_3Y$ in which Y is chosen from Li, Na, K, $NH_4^\oplus$, $NR''_4^\oplus$ in which R" represents a hydrocarbon-based radical that may contain from 1 to 15 carbon atoms; and Z represents a hydrocarbon-based radical containing 2 or 3 carbon atoms;

R represents a hydrocarbon-based radical of valency a; on condition that at least one of the radicals Z and R bears at least one electron-withdrawing substituent.

Advantageously, Z contains 2 carbon atoms and R is chosen from alkyl, cycloalkyl, aryl, alkylaryl and arylalkyl radicals, each generally containing from 1 to 20 carbon atoms and preferably from 1 to 10 carbon atoms, Z is preferably unsaturated.

Preferably, the catalyst corresponds to the following formula:

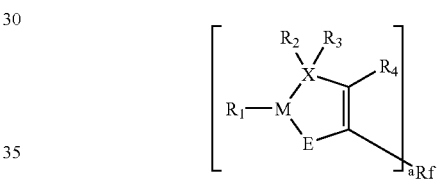

in which:

E, X, M, a, $R_1$, $R_2$ and $R_3$ have the same meanings as above;

Rf represents a hydrocarbon-based radical of valency a and bearing said electron-withdrawing substituent(s); and $R_4$, as for $R_1$, $R_2$ and $R_3$, may be chosen from hydrogen, alkyl, cycloalkyl, aryl, alkylaryl and arylalkyl radicals, each generally containing from 1 to 20 carbon atoms, the hydroxyl radical, alkoxide radicals (with from 1 to 20 carbon atoms), —C(O)OR' in which R' represents a hydrocarbon-based radical that may contain from 1 to 15 carbon atoms, —$SO_3Y$ in which Y is chosen from Li, Na, K, $NH_4^\oplus$, $NR''_4^\oplus$ in which R" represents a hydrocarbon-based radical that may contain from 1 to 15 carbon atoms.

The Applicant has found, surprisingly, that the substituent Rf allows the catalyst according to the invention to be markedly more active than the catalytic systems of the prior art.

The hydrocarbon-based radical Rf may be a radical chosen from alkyl, cycloalkyl, aryl, alkylaryl and arylalkyl radicals, generally containing from 1 to 20 carbon atoms and preferably from 1 to 10 carbon atoms.

The electron-withdrawing substituent borne by Rf may be chosen from halogens and —CN, $NO_2$, $NH^{3+}$, C≡Cr, CH=$CR'''_2$, COR''', $SO_2R'''$, $NR'''_3^+$, $SR'''_2^+$ and $SO_2Ar$ groups, R''' representing an alkyl group containing from 1 to 20 and preferably from 1 to 7 carbon atoms, and Ar representing an aryl group, preferably a phenyl group.

Preferably, the electron-withdrawing substituent is chosen from the group consisting of fluorine, chlorine, bromine, iodine and a nitro group.

Even more preferably, the electron-withdrawing substituent is a fluorine atom. Advantageously, the radical Rf is perfluorinated.

The radicals $R_1$, $R_2$, $R_3$ and $R_4$, which may be identical or different, may be chosen from hydrogen, alkyl, cycloalkyl, aryl, alkylaryl and arylalkyl radicals, each generally containing from 1 to 20 carbon atoms, preferably from 1 to 10 carbon atoms, halogens, the hydroxyl radical, alkoxide radicals (with from 1 to 20, preferably 1 to 10 carbon atoms), —C(O)OR' in which R' represents a hydrocarbon-based radical that may contain from 1 to 15, preferably 1 to 6 carbon atoms, —SO$_3$Y in which Y is chosen from Li, Na, K, $NH_4^\oplus$, $NR''_4^\oplus$ in which R" represents a hydrocarbon-based radical that may contain from 1 to 15 carbon atoms and preferably from 1 to 7 carbon atoms. Advantageously, the radicals $R_1$, $R_2$ and $R_3$ are chosen from aryl groups, in particular phenyl. Advantageously, the radical $R_4$ is a group —C(O)OR' in which R' represents a hydrocarbon-based radical that may contain from 1 to 6 carbon atoms.

According to one embodiment of the invention, at least one of the radicals $R_1$, $R_2$, $R_3$ and $R_4$ may optionally be a radical such as the radical Rf defined above.

Preferably, M is a nickel atom.

Preferably, E is an oxygen atom.

Preferably, X is a phosphorus atom.

The catalysts may be in the form of bimetallic complexes. Mention may be made in particular of those in which a is 2 and $R_4$ is a group —COOR, R being an alkyl containing from 1 to 7 carbon atoms. Such catalysts have the formula:

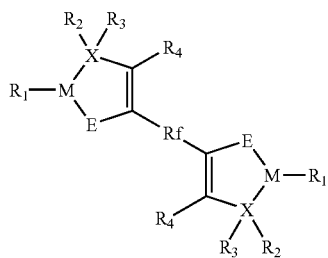

The catalysts that have been found to be the most advantageous are those for which a is 1, the groups $R_1$, $R_2$ and $R_3$ are a phenyl group, $R_4$ is the group —COOR', with R' which is an alkyl containing 1 to 7 carbon atoms or an aryl radical; X is a phosphorus atom, E is an oxygen atom and Rf is a fluorinated alkyl or aryl radical.

Advantageously:

R' is an ethyl, tert-butyl or benzyl group, in which case Rf is a pentafluorophenyl; or R' is an ethyl group and Rf is a trifluoromethyl group; or R' is an ethyl group and Rf is a heptafluoropropyl group.

Preparation of the Catalyst According to the Invention

The catalyst according to the invention may be prepared according to a process involving a step in which a compound corresponding to the formula below (constituent A) is reacted with a derivative of the metal M as defined above (in state 0), represented by M(0), (constituent B), so as to obtain the catalyst. When the metal M is nickel, NiCOD (in fact Ni(COD)$_2$) may then be used as derivative of the metal M, the term COD representing cis,cis-1,5-cyclooctadiene. The scheme is then as follows:

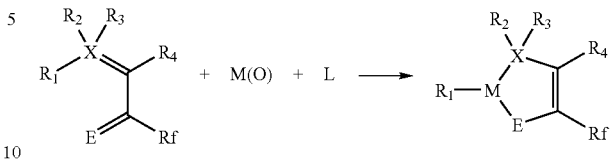

L is a ligand generally chosen from the phosphines of formula $PR^{14}R^{15}R^{16}$ in which $R^{14}$, $R^{15}$ and $R^{16}$, which may be identical or different, may represent alkyl, aryl, alkylaryl or arylalkyl radicals, or from phosphine oxides, ethers, esters, nitrites, ketones, amines, pyridine, substituted pyridines and alcohols.

According to one variant, the ligand L is an olefin.

It is possible to prepare the catalyst according to the invention via two main routes.

The first route involves a separation of the catalytic species before performing the polymerization. This approach is described in document U.S. Pat. No. 4,716,205. The catalytic species may be isolated either complexed with a Lewis base (ligand L=phosphine of formula $PR^{14}R^{15}R^{16}$ as defined above, or pyridine) or in dimer form.

If the ligand is strongly coordinated to the metal ($PPh_3$), it is desirable, in order to polymerize, to use a "phosphine sponge" in order to avoid any possible competition between the ligand and the monomer. If the ligand is more weakly coordinated (pyridine or dimer), this "phosphine sponge" is not preferred. This term "phosphine sponge" covers the corresponding term "scavengers".

The second route uses the in situ preparation of the catalyst.

The catalytic species is formed in situ by introducing the ylide and the Ni(0) complex into the reactor in the presence of an olefin.

Polymerization Process According to the Invention

The catalyst according to the invention is intended to be used for the polymerization of at least one olefin.

Preferably, the olefin(s) is (are) acyclic.

Ethylene or propylene is polymerized in particular.

The polymerization medium may comprise a liquid aqueous phase.

The catalyst according to the invention may advantageously be used in a medium comprising more than 30% water.

According to a first variant, the catalyst is prepared and a (co)polymerization is then performed, which takes place at a temperature of between 0 and 300° C. and preferably between 25 and 250° C., and at a total absolute pressure ranging from 1 to 200 bar and preferably from 1 to 100 bar. Variants of this embodiment (solvent, temperature, additives, etc.) are given in the following description, with regard to the second preferred embodiment of the invention.

According to this second embodiment, the process involves:

in a first step, introducing into a reactor, separately or simultaneously, each of the constituents (A) and (B) dissolved in an inert solvent, and also the reaction medium; and in a second step, introducing the olefin(s), the (co)polymerization taking place at a temperature of between 0 and 300° C., and preferably between 25 and 250° C., and at a total absolute pressure ranging from 1 to 200 bar, and preferably from 1 to 100 bar.

The inert solvent containing the constituents (A) and (B) for the first step is a solvent that is compatible with the operations to be conducted. Examples of such solvents that may be mentioned include any solvent that is compatible with the polymerization of olefins via organometallic catalysis, in particular saturated aliphatic hydrocarbons, saturated alicyclic hydrocarbons, aromatic hydrocarbons, for instance isobutane, butane, pentane, hexane, heptane, isododecane, cyclohexane, cycloheptane, methylcyclohexane, methylcycloheptane, benzene, toluene, ortho-xylene and para-xylene, and any mixture of the above compounds.

The inert solvents for each of the constituents (A) and (B) may be identical or different.

The reaction medium of the process according to the invention may consist of an organic medium, or it may comprise a continuous liquid aqueous phase, which comprises more than 30% by weight of water. In the latter case, the aqueous phase may be the only liquid phase of the reaction medium (except for the solutions of the constituents (A) and (B)). Also in this case, the medium may comprise a liquid organic phase.

The concentration of constituent (A) in the inert solvent is preferably between 0.1 micromol and 100 millimol per liter of solution; and the concentration of constituent (B) in the inert solvent is preferably between 0.1 micromol and 200 millimol per liter of solution.

The process according to the invention is generally performed under an inert atmosphere.

In a preliminary step, the constituents (A) and (B) dissolved in their inert solvent may be placed in contact for a period of less than 15 minutes, before introducing them into the reaction medium, this precontact step also being performed under an inert atmosphere, at a temperature of between 0 and 100° C., in particular between 10 and 70° C.

The constituents (A) and (B) that are dissolved in their inert solvent may also be introduced separately in any order into the reaction medium, said medium being maintained at a temperature from 0 to 100° C. and in particular from 10 to 70° C.

The polymerization medium (organic medium) or the organic phase of a polymerization medium comprising a liquid aqueous phase may be chosen from:

saturated aliphatic hydrocarbons, saturated alicyclic hydrocarbons and aromatic hydrocarbons, and mixtures thereof, in particular from isobutane, butane, pentane, hexane, heptane, isododecane, cyclohexane, cycloheptane, methylcyclohexane, methylcycloheptane, benzene, toluene, ortho-xylene, and para-xylene, and any mixture of these compounds; and provided that the polymerization conditions keep them in liquid form, α-olefins, such as propylene, butene, hexene or 4-methyl-1-pentene, nonconjugated dienes, such as 1,9-decadiene, 1,5-hexadiene, 1,13-tetradecadiene and biscyclo[2.2.1]hepta-2,5-diene, and mixtures thereof.

When the polymerization medium comprises an aqueous phase, during the polymerization, the polymerization medium comprises said liquid aqueous phase, a solid phase consisting of the solid polymer obtained from the polymerization, and also comprises, depending on the physical state of the olefin to be polymerized, at least one other gaseous phase and/or one other liquid phase. If an olefin to be polymerized is liquid under the polymerization temperature and pressure conditions, this olefin may form part of a liquid organic phase that is separate (distinct) from the liquid aqueous phase. Such a liquid organic phase may also comprise an organic solvent, such as those indicated above, for said olefin.

The constituents of the optional liquid organic phase are sufficiently water-insoluble that, given the amount thereof used, the aqueous phase contains more than 30% water.

For the case in which the polymerization medium comprises two separate liquid phases, these phases may, for example, be present such that the phase different than the aqueous phase represents 1% to 50% of the volume of the aqueous phase.

The aqueous phase may comprise at least 40%, or even at least 50%, or even at least 60%, or even at least 70%, or even at least 80%, by weight of water.

The aqueous phase may comprise in dissolved form an organic compound that may be an alcohol, a ketone or a diol such as a glycol, for example ethylene glycol, propanediol or butanediol. This organic compound may serve to increase the solubility of the olefin to be polymerized in the aqueous phase.

The polymerization medium is preferably stirred. The stirring is preferably sufficient to distribute the various phases uniformly in the reactor.

At least one dispersant may be added to the polymerization medium. Such a dispersant may be used in particular when the polymerization medium comprises a liquid organic phase, in which case it aids the dispersion of said liquid organic phase in the form of droplets surrounded by the continuous aqueous phase. In this case, since the constituents (A) and (B) have mainly been dissolved in the liquid organic phase, the polymerization mainly takes place in the droplets, these droplets generally having a mean diameter of between 100 μm and 3 millimeters.

The dispersant may be any of those known to have this function, such as, for example, a polyvinyl alcohol, methylcellulose, a gelatin, kaolin, barium sulfate, hydroxyapatite, magnesium silicate, tricalcium phosphate, or a combination of several of these dispersants.

The dispersant may be introduced into the polymerization medium at up to 10% by weight relative to the weight of water used, and preferably from 0.01% to 5% by weight relative to the weight of water used.

At least one emulsifier may be added to the polymerization medium. The use of such an emulsifier is recommended in particular when it is desired for the polymerization to lead to a latex, i.e. a combination of polymer particles with a number-average diameter of less than 1 micrometer, said particles being dispersed in the aqueous phase. When an emulsifier is used, it is generally not necessary for the polymerization medium to contain a dispersant.

Emulsifiers that may be used include any known surfactant, whether anionic, nonanionic or even cationic. In particular, the emulsifier may be chosen from anionic surfactants such as the sodium or potassium salts of fatty acids, especially sodium laurate, sodium stearate, sodium palmitate, sodium oleate, mixed sulfates of sodium or of potassium and of fatty alcohol, especially sodium lauryl sulfate, the sodium or potassium salts of sulfosuccinic esters, the sodium or potassium salts of alkylarylsulfonic acids, especially sodium dodecylbenzenesulfonate, and the sodium or potassium salts of fatty monoglyceride monosulfonates, or alternatively from nonionic surfactants such as the products of reaction between ethylene oxide and alkylphenols. Needless to say, mixtures of such surfactants may be used.

The emulsifier may be introduced into the polymerization medium at up to 10% by weight relative to the weight of water and preferably from 0.01% to 5% by weight relative to the weight of water.

In such a process comprising an emulsifier and a liquid organic phase, since the constituents (A) and (B) have mainly been dissolved in said liquid organic phase, the emulsifier being in an amount greater than the critical micelle concentration, the polymerization takes place in the droplets of liquid organic phase, which generally have a mean diameter of between 1 mm and 1 000 mm, and in the micelles which generally have a mean diameter of between 1 nanometer and 100 nanometers. Such a process is similar to the "free-radical emulsion polymerization" process, except that it is not free-radical-mediated. When, in such a process, the emulsifier concentration is increased, the relative magnitude of the polymerization taking place in the micelles is increased and the formation of a latex at the end of polymerization is promoted. In this case of a liquid organic phase being present, when the amount of emulsifier is such that all the liquid organic phase is present in the micelles, the process is similar to the "free-radical microemulsion polymerization" process, except that the polymerization is not free-radical-mediated.

For the case in which the polymerization medium comprises a liquid organic phase and an emulsifier, it is possible to add to the medium a cosurfactant, as is performed for miniemulsion polymerization processes. Such a cosurfactant generally has a water solubility of less than $1 \times 10^{-3}$ mol per liter at 20° C. Such a cosurfactant may be, for example, hexadecane or cetyl alcohol. It may be present at up to 10% by weight relative to the weight of water, and the ratio of the mass of emulsifier to that of cosurfactant preferably ranges from 0.5 to 2. The presence of this cosurfactant makes it possible, also by means of a sufficient shear of the medium, to obtain droplets of liquid organic phase of less than 1 mm and to promote the formation of a latex at the end of polymerization. The sufficient shear may be obtained, for example, by ultrasonication or using a homogenizer (for instance a machine of the Ultra-Turrax or Diax 600 type from the company Heidolph). Once the characteristic size of the droplets (<1 mm) is obtained, the stirring may be continued with a less vigorous shear, of the type of shears used for suspension polymerization processes.

The polymerization is preferably performed in miniemulsion.

For the case in which an organic solvent has been used, it may be removed, if so desired, by evaporation.

The process according to the invention leads to polymer particles with a diameter that may range from 10 nanometers to 5 millimeters.

When the polymerization comprises an emulsifier, a latex is obtained. After the polymerization performed in the presence of an emulsifier, the latex possibly contains particles that have a tendency to separate out by settling, and it may be desired to perform a separation, for example by filtration, so as to remove these particles not forming part of the latex.

The polymerization conditions, i.e. the amount of the ingredients in the polymerization medium and the degree of conversion of monomer to polymer, may be adapted such that the latex has a solids content ranging from 0.1% to 50% by weight.

The olefin intended to be polymerized is introduced with sufficient stirring of the polymerization medium, for example stirring ranging from 10 to 10 000 rpm. The olefin may be introduced in liquid or gaseous form, depending on its physical state.

The polymerization temperatures and pressures have been indicated above.

When only ethylene is polymerized, a high-density homopolyethylene is obtained. The polymerization of ethylene with at least one olefin other than ethylene leads to the production of an ethylene polymer of lower density than the high-density homopolyethylene mentioned above. Depending on the amount and nature of the ethylene comonomer(s), it is thus possible to obtain a high-density ethylene polymer (high-density polyethylene), or a medium-density ethylene polymer (medium-density polyethylene) or even, at a high comonomer content, a low density ethylene polymer (low-density polyethylene).

As is common for ethylene polymers, the term "high density" means that the density is greater than 0.940, "medium density" means that the density ranges from 0.925 to 0.940, and "low density" means that the density is less than 0.925.

The polymerization may thus lead to a latex of at least one olefin, i.e. a polymer comprising polymerized units of at least one olefin, where appropriate with other units of polymerized monomer. In particular, if at least one olefin is ethylene, a latex of an ethylene polymer may be obtained.

The process according to the invention may thus lead to a latex of a high-density ethylene polymer or to a latex of a medium-density ethylene polymer, or even of a low-density ethylene polymer.

In the context of the present patent application, the term "polymer" must be understood in its general sense, such that it covers homopolymers, copolymers, inter-polymers and polymer blends. The term "polymerization" must also be taken in equivalent general sense.

The combination of olefins comprises that of α-olefins. Olefins that may be mentioned include ethylene, propylene, cyclopentene, 1-hexene, 3-methyl-1-pentene, 4-methyl-1-pentene, 1,4-hexadiene, 1,9-decadiene, 1-octene, 1-decene, and cyclic olefins, for instance cyclohexene. The combination of olefins also includes compounds of formula $CH_2{=}CH(CH_2)_nG$ in which n represents an integer ranging from 2 to 20 and G represents a radical that may be chosen from the following list:

OH, CHOHCH$_2$OH, OT, CF$_3$, COOT, COOH, Si(OH)$_3$, Si(OT)$_3$, T representing a hydrocarbon-based radical containing from 1 to 20 carbon atoms. Mention is made in particular of the cases in which at least one olefin is ethylene.

The process according to the invention may be performed in batch mode, in semicontinuous mode or in continuous mode).

EXAMPLES

The examples that follow illustrate the present invention without, however, limiting its scope. In these examples, the synthetic scheme is as follows:

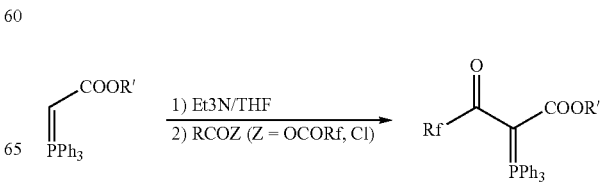

-continued

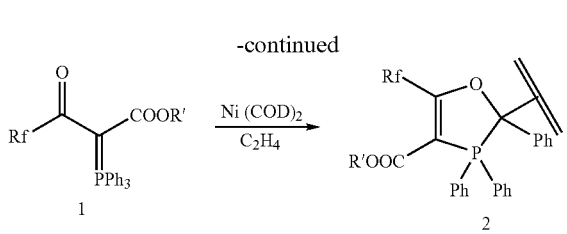

The following compounds are prepared:

| Compound | Rf | R[1] |
|---|---|---|
| 1a | $CF_3$ | Et |
| 1b | $C_3F_7$ | Et |
| 1c | $C_6F_5$ | Et |
| 1d | $C_6F_5$ | tert-Bu |
| 1e | $C_6F_5$ | Bn |
| 1f | $CH_3$ | Et |
| 1g | $C_6H_5$ | Et |

Examples 1 to 4

Preparation of the Compounds (Ligands 1b to 1e)

Example 1

Synthesis of ethyl 6,6,6,5,5,4,4-heptafluoropropyl-3-oxo-2-(triphenylphosphoranylidene)hexanoate A suspension of carbethoxymethyltriphenylphosphonium bromide (3.4 g, 7.9 mmol) in 25 ml of anhydrous THF is cooled in an ice bath and treated with triethylamine (2.4 ml, 17.2 mmol). After stirring for 15 minutes, the mixture is treated by dropwise addition of heptafluorobutyryl chloride (1.28 ml, 8.6 mmol). The temperature is allowed to return to room temperature and the mixture is left to stand for a further one hour. The reaction mixture is then filtered and the precipitate is washed three times with cold THF, and the filtrate is dried under vacuum. The powder obtained is recrystallized from methanol. The yield is 63%.

$^1$H NMR (ppm, in $CDCl_3$): $C_6H_5$ 7.4–7.8, 15H, m; $OCH_2$, 3.78, 2H, q; $CH_3$, 0.9, 2H, t (3JH-H=7 Hz). 13C (ppm, in $CDCl_3$) 13.6, 60.3, 72.6 (1JC-P=115 Hz), 124 (1JC-P=100 Hz), 129.9 (2JC-P=13 Hz), 132.6 (4JC-P=3 Hz), 133.4 (3JC-P=10 Hz), 165.7 (2JC-P=13.5 Hz), 175.2 (2JC-F=27 Hz, 2JC-P=6 Hz).

$^{19}$F NMR (ppm, in $CDCl_3$) $COCF_2$ −124.9, s; $CF_2$−113.7, q (3JF-F=1.5 Hz); $CF_3$ −80.7, t (3JF-F=1.5 Hz).

$^{31}$P NMR (ppm, in $CDCl_3$), 20, s.

IR (10% KBr granule): 3062, 2981, 1709, 1682, 1579, 1571, 1486, 1437, 1330, 1251, 1234, 1200, 1157, 1105, 968, 935, 757, 692, 556, 516 $cm^{-1}$.

Elemental analysis: C calculated: 57.36%, found 57.61%. H calculated: 3.70%, found 3.87%.

Example 2

Synthesis of Ethyl Pentafluorobenzyl-3-oxo-2-(tri-phenylphosphoranylidene)propanoate The process is performed as in example 1, with (ethoxycarbonylmethyl)triphenylphosphonium bromide (0.8 g, 2.0 mmol), triethylamine (0.6 ml, 4.2 mmol) and pentafluorobenzoyl chloride (0.3 ml, 2.1 mmol). The yield is 52%.

$^1$H NMR (ppm, in $CDCl_3$) $C_6H_5$ 7.5–7.6 and 7.7–7.8, 15H, m; $OCH_2$, 3.65, 2H, q; $CH_3$, 0.58, 2H, t (3JH-H=7 Hz). 13C (ppm, in $CDCl_3$) 13.5, 58.9, 74.2 (1JC-P=110 Hz), 124.7 (1JC-P=94 Hz), 128.8 (2JC-P=13 Hz), 132.4 (4JC-P=3 Hz), 133.5, (3JC-P=10 Hz), 166.7 (2JC-P=13 Hz), 178.7 (2JC-P=7 Hz).

$^{19}$F NMR (ppm, in $CDCl_3$) $C_6F_5$ −145.2 dd (3JF-F=22 Hz, 4JF-F=6.7 Hz), −175.8, t (3JF-F=22 Hz), −163.7, td (3JF-F=22 Hz, 4JF-F=6.7 Hz).

$^{31}$P NMR (ppm, in $CDCl_3$), 18.3 s. IR: 1661, 1562, 1517, 1496, 1437, 1369, 1341, 1293, 1244, 1103, 1087, 983, 940, 692, 542 $cm^{-1}$. Elemental analysis: C calculated: 64.21%, found: 64.49%. H calculated 3.72%, found 3.84%.

Example 3

Synthesis of tert-butyl pentafluorobenzyl-3-oxo-2-(triphenylphosphoranylidene)propanoate The process is performed as in example 1, with (tert-butoxycarbonylmethyl)triphenylphosphonium bromide (1.65 g, 4.0 mmol), triethylamine (1.3 ml, 8.2 mmol) and pentafluorobenzoyl chloride (0.6 ml, 4 mmol). The yield is 62%.

$^1$H NMR (ppm, in $CDCl_3$) $C_6H_5$ 7.4–7.9, 15H, m; $CH_3$, 0.96, 9H, s., 13C (ppm, in $CDCl_3$) 13.5, 58.9, 74.2 (1JC-P=110 Hz), 124.7 (1JC-P=94 Hz), 128.8 (2JC-P=13 Hz), 132.4 (4JC-P=3 Hz), 133.5 (3JC-P=10 Hz), 166.7 (2JC-P=13 Hz), 178.7 (2JC-P=7 Hz), $^{19}$F NMR (ppm, in $CDCl_3$) $C_6F_5$ −145.2, dd (3JF-F=22 Hz, 4JF-F=7.4 Hz), −158.0, t (3JF-F=22 Hz), −163.8, td (3JF-F=22 Hz, 4JF-F=7.4 Hz).

$^{31}$P NMR (ppm, in $CDCl_3$), 18.1, s. IR: 1666, 1552, 1516, 1495, 1437, 1359, 1303, 1247, 1167, 1108, 988, 941, 692, 543, 521 $cm^{-1}$.

Elemental analysis: C calculated: 65.27%, found 65.28%. H calculated 4.24%, found 4.31%.

Example 4

Synthesis of benzyl pentafluorobenzyl-3-oxo-2-(tri-phenylphosphoranylidene)propanoate The process is performed as in example 1, with (benzyloxycarbonylmethyl)triphenylphosphonium bromide (0.98 g, 2.0 mmol), triethylamine (0.58 ml, 4.2 mmol) and pentafluorobenzoyl chloride (0.3 ml, 2.1 mmol). The yield is 32%.

$^1$H NMR (ppm, in $CDCl_3$) $C_6H_5$, 20H, m; $CH_2$, 2H, s. 13C (ppm, in $CDCl_3$) 65.7, 74.4 (1JC-P=112 Hz), 124.5 (1JC-P=94 Hz), 128.0, 128.2, 128.5, 128.8 (2JC-P=13 Hz), 132.4 (4JC-P=3 Hz), 133.5 (3JC-P=10 Hz), 135.6, 166.3 (2JC-P=13 Hz), 178.7 (2JC-P=7 Hz), $^{19}$F NMR (ppm, in $CDCl_3$) $C_6F_5$ −145.7, dd (3JF-F=23 Hz, 4JF-F=7 Hz), −157.4, t (3JF-F=23 Hz), −163.8, td (3JF-F=23 Hz, 4JF-F=7 Hz).

$^{31}$P NMR (ppm, in $CDCl_3$), 18.6, s.

IR: 1648, 1554, 1519, 1487, 1440, 1341, 1288, 1274, 1066, 986, 754, 690, 545, 510, 501 $cm^{-1}$. Elemental analysis: C calculated: 67.55%, found 67.32%. H calculated 3.67%, found 3.95%.

Example 5 a) Preparation of the Polymerization Catalyst 1a 23.5 mg of $Ni(COD)_2$ are dissolved in 8.5 ml of toluene in a Schlenk tube. 4 ml of the solution obtained are added to 8.9 mg of commercial ethyl trifluoromethyl-3-oxo-2-(triphenylphosphoranylidene)hexanoate (1a). The solution is stirred for 15 minutes and 0.6 ml of this solution is added to 400 ml of toluene in a glass reactor.

b) Polymerization

The solution obtained above is introduced into a 1 liter stainless-steel reactor equipped with a mechanical stirrer with magnetic induction, a thermocouple, a sampling orifice and a jacket, and heated to 70° C.

Ethylene is immediately introduced at a pressure of 3 bar. The introduction of ethylene is continued without interruption at a pressure of 3 bar from a 1 liter tank under high pressure. The pressure drop in the tank is recorded, so as to evaluate the activity and to measure the production efficiency. The reaction medium (about 400 ml) is added to about 600 ml of methanol and about 70 g of polymer are then recovered by filtration.

Another polymerization test was performed with a larger amount of catalyst 1a. The characteristics of the polymerization are given in table 1.

Example 6

Polymerization catalysts 1b to 1e are prepared, as described in example 5, in a), starting with the ligands of examples 1 to 4, respectively.

Polymerization catalysts 1f and 1g are also prepared, in the same manner, according to the abovementioned French patent application 2 784 110, starting with ethyl methyl-3-oxo-2-(triphenylphosphoranylidene)hexanoate and ethyl benzyl-3-oxo-2-(triphenylphosphoranylidene)propanoate, respectively. These two acids were obtained commercially.

Polymerizations 1 to 13 were then performed, according to the procedure described in example 5, in b). The characteristics of these polymerizations 1 to 13 are given in table 1 below.

Except where otherwise mentioned in table 1, the polymerizations were performed with the catalyst in 400 ml of toluene under 3 bar of ethylene and at 70° C.

ethyl-3-oxo-2-(triphenylphosphoranylidene)hexanoate are added to the solution. The solution is stirred for 15 minutes.

b) Polymerization

The solution obtained above is added to 300 ml of water containing 5 g/l of sodium lauryl sulfate (surfactant) in a Teflon round-bottomed flask.

To perform a miniemulsion polymerization, hexadecane (10 g per liter of water) is added to the two-phase mixture obtained and the mixture is emulsified using an ultrasonicator such as a Branson 600 W machine for 2 minutes, with magnetic stirring and under argon. As a variant, a homogenization may be performed for 10 minutes using an Ultra-Turrax machine.

Next, the reaction medium (fine dispersion in the case of a miniemulsion and two-phase mixture in the case of an emulsion) is introduced into a 1 liter stainless-steel reactor equipped with a mechanical stirrer (magnetic), a thermocouple, a sampling orifice and a jacket heated to 70° C.

Ethylene is immediately introduced at a pressure of 20 bar. The introduction of ethylene is continued without interruption at a pressure of 20 bar from a 5.5 liter reservoir at high pressure. The drop in pressure in the reservoir is recorded, so as to evaluate the activity and to measure the production efficiency. The reaction medium (300 ml) is recovered after the remaining ethylene has been stripped off, slowly enough to avoid the flocculation of a latex by creamy sedimentation. The latex is filtered to determine the floc content, and the liquid residue is analyzed by dynamic light scattering (DLS) and gravimetry.

Example 8

Polymerization catalysts 2b to 2e are prepared, as described in example 7, in a), starting with the ligands of examples 1 to 4, respectively.

Polymerization catalysts 2f and 2g according to the prior art are also prepared, in the same manner, starting with ethyl

TABLE 1

| Polymerization No. | Catalyst used | Amount of catalyst used (μmol) | Production efficiency (kg/g of Ni) | Activity (kg/g of Ni/h) | Mw[c] | Ratio Mw/Mn | Branches/ 1000 C |
|---|---|---|---|---|---|---|---|
| 1 | 1a | 2 | 272 | >2000 | 2438 | 3.1 | 0.8 |
| 2[b] | 1a | 3 | 102 | 970 | 2213 | 3.9 | 0.8 |
| 3 | 1b | 4 | 154 | 1400 | | | |
| 4 | 1c | 4.5 | 58 | 610 | | | |
| 5[b] | 1c | 3 | 58 | 420 | 2137 | 3.2 | 0.6 |
| 6 | 1d | 3 | 112 | 1180 | | | |
| 7[b] | 1d | 3 | 126 | 500 | 1716 | 3.7 | 0.7 |
| 8 | 1e | 3 | 100 | 1080 | | | |
| 9[b] | 1e | 3 | 64 | 560 | 1754 | 3.4 | 0.7 |
| 10[d] | 1b | 5 | 51 | 140 | | | |
| 11 | 1f | 45 | 2 | 8 | | | |
| 12 | 1g | 45 | 8 | 35 | | | |
| 13[e] | 1a | 10 | 1 | 15 | 1500 | 2.0 | |

[b]the reactions were performed in 400 ml of heptane
[c]values determined by gel permeation chromatography by comparison with polyethylene standards
[d]the solvent was a 300 ml/100 ml toluene/water mixture
[e]this is a polymerization of propylene rather than of ethylene

Example 7

Emulsion and Miniemulsion Polymerizations a) Preparation of the Polymerization Catalyst 2a 33 mg of Ni(COD)$_2$ are dissolved in 10 ml of toluene in a Schlenk tube. 13.3 mg of commercial ethyl trifluorommethyl-3-oxo-2-(triphenyl-phosphoranylidene)hexanoate and ethyl benzyl-3-oxo-2-(triphenylphosphoranylidene)propanoate, respectively.

The polymerizations are then performed according to the procedure described in example 7, in b), polymerizations 14 to 19 being performed in emulsion and polymerizations 20 to 36 in miniemulsion.

The characteristics of these polymerizations 14 to 26 are given in table 2 below.

TABLE 2

| Polymerization No. | Catalysts No. | Amount of toluene | Pressure (bar) | Temperature (° C.) | Activity (kg/g of Ni/h) | Production efficiency[h] (kg/g of Ni) |
|---|---|---|---|---|---|---|
| 14 | 2a | 400 | 3 | 70 | >2000 | 272 |
| 15 | 2a | 32 | 25 | 65 | 23 | — |
| 16 | 2b | 36 | 25 | 65 | 40 | — |
| 17 | 2c | 12 | 20 | 75 | 70 | — |
| 18 | 2c | 10 | 20 | 45 | 3 | — |
| 19 | 2d | 24 | 5 | 65 | 5 | — |
| 20[f] | 2d | 20 | 25 | 70 | 23 | 3 |
| 21 | 2e | 10 | 25 | 70 | 40 | 7 |
| 22 | 2e | 10 | 25 | 65 | 45 | 49 |
| 23 | 2b | 20 | 25 | 65 | 83 | 46 |
| 24 | 2f | 15 | 25 | 70 | 56 | 13 |
| 25[b] | 2g | 3 | 25 | 65 | 6 | 6 |
| 26[e] | 2a | 10 | 25 | 65 | 8 | 9 |

| Polymerization No. | Volume of water (ml) | Sodium lauryl sulfate concentration in g/l | Hexadecane concentration in g/l per liter of water | Particle size (nm)[c] | Solids content[d] (% by mass) | Floc (% by mass) |
|---|---|---|---|---|---|---|
| 14 | — | — | — | — | — | — |
| 15 | 500 | 2 | — | — | 0.35 | — |
| 16 | 500 | 20 | — | — | 1.98 | — |
| 17 | 500 | 5 | — | 850 | 0.95 | 98 |
| 18 | 500 | 5 | — | — | 0.52 | — |
| 19 | 500 | 5 | — | — | 0.50 | — |
| 20[f] | 500 | 5 | 12 | 606 ± 429[f] | 2.2 | Nm[g] |
| 21 | 500 | 5 | 8 | 242 ± 145 | 3.7 | Nm[g] |
| 22 | 800 | 5 | 10 | 242 ± 147 | 8.5 | Nm[g] |
| 23 | 500 | 5 | 10 | 208 ± 175 | 10.2 | Nm[g] |
| 24 | 500 | 3 | 6 | 366 ± 168 | 1.5 | Nm[g] |
| 25 | 300 | 1.5 | 3 | 410 ± 266 | 2.2 | Nm[g] |
| 26[e] | 300 | 1.5 | 3 | 467 ± 330 | 3.9 | Nm[g] |

[b]benzene is used instead of toluene
[c]values determined by dynamic light scattering (DLS) after dilution
[d]solids content determined by gravimetry of the latex after filtration
[e]the catalyst used is 2b
[f]emulsification performed with an Ultra-Turrax machine, at low speed
[g]not measurable (less than 3% polymer)
[h]production efficiency in the aqueous phase without taking the floc into account Example 9

This example presents, comparatively, the production efficiencies of catalysts of the prior art with catalysts 1a to 1e and 2a to 2e according to the invention.

The data are given in the following table:

| Catalysts (1) | Polymerization conditions | Production efficiency (kg polyethylene/g of Ni) |
|---|---|---|
| Cat. 1 | Toluene<br>P = 50 bar<br>T = 70° C. | 12.7 |
| Cat. 2 | Toluene<br>P = 5.2 bar<br>T = 66° C. (optimum conditions) | 23.2 |
| Cat. 3 | Toluene<br>P = 5.2 bar<br>T = 60° C. | 5.73 |
| Cat. 4 | Toluene<br>P = 14 bar<br>T = 50° C. | 3.32 |

-continued

| Catalysts (1) | Polymerization conditions | Production efficiency (kg polyethylene/g of Ni) |
|---|---|---|
| 1a to 1e and 2a to 2e | Toluene<br>P = 3 bar<br>T = 70° C. | From 51 to 272 |

(1):
Cat. 1 is catalyst No. 2a from the article entitled "Coordination polymerization of ethylene in water by Pd(II) and Ni(II) catalysts" by A. Held, F. M. Bauers and S. Mecking, Chem. Comm., 2000, 301–302;
Cat. 2 is catalyst No. 6 from the article entitled "Ethylene Homopolymerization with P, O-Chelated Nickel Catalysts" by U. Klabunde, et al., Journal of Polymer Science, Part A: Polymer Chemistry, Vol. 25, 1989–2003 (1987);
Cat. 3 is catalyst No. 8 from the article entitled "Ethylene Homopolymerization with P, O-Chelated Nickel Catalysts" by U. Klabunde, et al., Journal of Polymer Science, Part A: Polymer Chemistry, Vol. 25, 1989–2003 (1987);
Cat. 4 is catalyst No. 2 from table 1 ("table 1") of the abovementioned patent U.S. Pat. No. 4 529 554.

It is thus found that the production efficiency of the catalysts according to the invention is at least twice as high as that of the catalysts of the prior art.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The foregoing references are hereby incorporated by reference.

The invention claimed is:

1. A catalyst for polymerizing olefins, corresponding to the following formula:

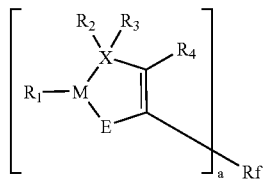

in which:
E is an oxygen or sulfur atom;
X is a phosphorus, arsenic or antimony atom;
M is a nickel, palladium or platinum atom comprising an unattributed valency;
a is 1 or 2;
$R_1$, $R_2$ and $R_3$, which may be identical or different, may be chosen from hydrogen, alkyl, cycloalkyl, aryl, alkylaryl and arylalkyl radicals, each generally containing from 1 to 20 carbon atoms, the hydroxyl radical, alkoxide radicals with from 1 to 20 carbon atoms, C(O)OR' in which R' represents a hydrocarbon-based radical that may contain from 1 to 15 carbon atoms, —$SO_3Y$ in which Y is chosen from Li, Na, K, $NH_4$, $NR_4$ in which R represents a hydrocarbon-based radical that may contain from 1 to 15 carbon atoms;
Rf represents a pentafluorophenyl, trifluoromethyl or heptafluoropropyl group; and
$R_4$ is a group —C(O)OR' wherein R' is an ethyl, tert-butyl or benzyl group, further wherein: when R' is an ethyl, tert-butyl or benzyl group, Rf is a pentafluorophenyl group; and when R' is an ethyl group, Rf is a trifluoromethyl group or a heptafluoropropyl group.

2. The catalyst as claimed in claim 1, wherein M is a nickel atom.

3. The catalyst as claimed in claim 1, wherein E is an oxygen atom.

4. The catalyst as claimed in claim 1, wherein X is a phosphorus atom.

5. The catalyst as claimed in claim 1, wherein the radicals $R_1$, $R_2$ and $R_3$ are selected from aryl groups.

6. The catalyst as claimed in claim 5, wherein the radicals $R_1$, $R_2$ and $R_3$ are phenyl groups.

7. The catalyst as claimed in claim 1, wherein a is 1.

8. The catalyst as claimed in claim 1, wherein
E is an oxygen atom;
X is a phosphorus atom;
M is a nickel atom;
a is 1; and
the radicals $R_1$, $R_2$ and $R_3$ are phenyl groups.

9. A process for polymerizing at least one olefin, comprising placing said olefin(s) in contact with a catalyst as claimed in claim 1.

10. A process for polymerizing at least one olefin, comprising placing said olefin(s) in contact with a catalyst as claimed in claim 8.

11. The process as claimed in claim 9, wherein the olefin is acyclic.

12. The process as claimed in claim 10, wherein the olefin is acyclic.

13. The process as claimed in claim 10, wherein the olefin is ethylene or propylene.

14. The process as claimed in claim 11, wherein the olefin is ethylene or propylene.

15. The process as claimed in claim 9, wherein the polymerization medium comprises a liquid aqueous phase.

16. The process as claimed in claim 10, wherein the polymerization medium comprises a liquid aqueous phase.

17. The process as claimed in claim 15, wherein the medium comprises more than 30% water.

18. The process as claimed in claim 16, wherein the medium comprises more than 30% water.

19. The process as claimed in claim 9, wherein:
prior to placing said olefin(s) in contact with said catalyst, the catalyst is prepared by a method comprising introducing, separately or simultaneously, constituent (A), constituent (B) and a reaction medium into a reactor, each of the constituents (A) and (B) being dissolved in an inert solvent, the constituent (A) corresponding to formula II below while the constituent (B) is a metal derivative M(0):

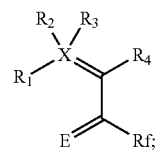

further wherein after placing said olefin(s) in contact with said catalyst, the polymerization or copolymerisation is carried out at a temperature of between 0 and 300°C., and at a total absolute pressure ranging from 1 to 200 bar.

20. A process for preparing a catalyst as claimed in claim 1, comprising reacting constituent (A) corresponding to formula II below:

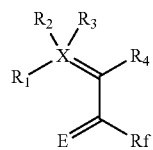

with a metal derivative M(0) and a ligand L according to a reaction scheme set forth below:

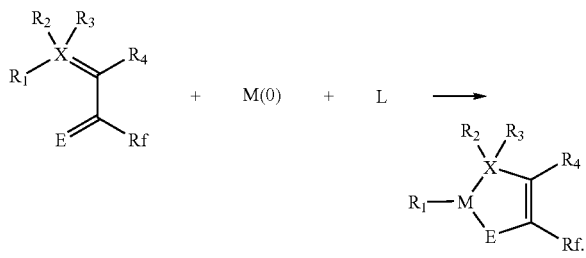

21. The process as claimed in claim 20, wherein L is an olefin.

22. The process as claimed in claim 21, wherein the temperature is between 25 and 250°C. and the absolute pressure is from 1 to 100 bar.

* * * * *